United States Patent [19]

Bridger

[11] Patent Number: 4,600,543

[45] Date of Patent: Jul. 15, 1986

[54] METHOD OF PREPARING ORGANIC AMMONIUM DIALKYL PHOSPHORODITHIOATES

[75] Inventor: Robert F. Bridger, Hopewell, N.J.

[73] Assignee: Mobil Oil Corporation, New York, N.Y.

[21] Appl. No.: 642,928

[22] Filed: Aug. 21, 1984

[51] Int. Cl.$^4$ ................................................ C07F 9/18
[52] U.S. Cl. ...................................... 558/133; 558/87
[58] Field of Search ....................... 260/987, 925, 921

[56] References Cited

U.S. PATENT DOCUMENTS 2,647,140  7/1953  Jonas .................................... 260/987

*Primary Examiner*—Anton H. Sutto
*Attorney, Agent, or Firm*—Alexander J. McKillop; Michael G. Gilman; Van D. Harrison, Jr.

[57] ABSTRACT

A process for making an organicammonium dialkyl phosphorodithioate has been discovered which involves a critical order of reactant addition. Thus it is essential to the process that the amine be added to a mixture of phosphonate and elemental sulfur.

14 Claims, No Drawings

METHOD OF PREPARING ORGANIC AMMONIUM DIALKYL PHOSPHORODITHIOATES

BACKGROUND OF THE INVENTION

1. Field of the Invention

The application relates to a process for making lubricant additives. In particular, it relates to a process for making a diorganicammonium phosphorothioate.

2. Discussion of the Prior Art

The organicammonium diaryl phosphorothioates are well known materials, useful as ashless antiwear additives in lubricants and other industrial oils. There are methods known to those skilled in the chemical arts for making the compounds, but they are generally complex and give low yields of product. One prior art method involves the following scheme, using, for example, phenol, thiophosphoryl chloride and butylamine:

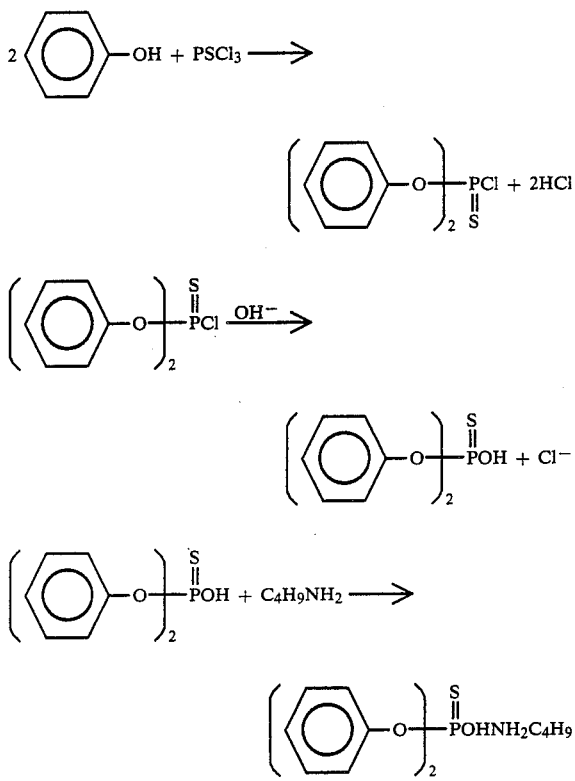

In contrast, my process is straightforward and provides products of excellent quality in nearly quantitative yields. It has, among others, the advantage that I can prepare the diaryl phosphonate in excellent yields by the conventional process in which phenol is reacted with phosphorus trichloride.

SUMMARY OF THE INVENTION

In accordance with the invention, the art is provided with a process for preparing a compound of the formula

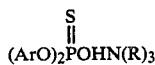

wherein Ar is an aromatic group or an aliphatic-substituted aromatic group containing 6 to 20 carbon atoms, in which the ring contains 6 to 10 carbon atoms, and R is hydrogen or a $C_1$ to $C_{20}$ hydrocarbyl group, at least one of the R groups being a hydrocarbyl group, said process comprising the steps of mixing a diaryl phosphonate of the formula

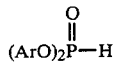

wherein Ar has the meaning herein, with elemental sulfur or a sulfur compound and reacting the mixture with an amine of the formula

wherein R is defined hereinabove. "Hydrocarbyl" as used herein, includes alkyl, cycloalkyl, alkenyl and cycloalkenyl, with alkyl being preferred. Sulfur compounds that may be used in the reaction include the polysulfides, such as the alkali metal or alkaline earth metal polysulfides, sulfurized olefins and the like. "Aliphatic" is preferably an alkyl group containing 1 to 14 carbon atoms. Included among the useful alkyl groups are methyl, ethyl, butyl, hexyl, octyl, decyl, dodecyl and tetradecyl.

DESCRIPTION OF SPECIFIC EMBODIMENTS

The process of this invention involves reacting a mixture of a diaryl phosphonate and sulfur with a primary, secondary or tertiary hydrocarbylamine containing 1 to 20 carbon atoms, preferably alkylamine. The reaction is shown in the following equation:

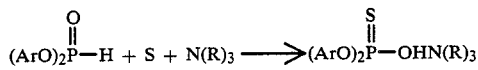

where "S" represents elemental sulfur or sulfur in compound form, which compound is capable of forming the P=S bond. The reaction is carried out at from about 25° C. to about 175° C., preferably about 90° C. provided that when elemental sulfur is used, the temperature of reaction will range from about 115° C. to about 175° C.

Preferably approximately equimolar portions of reactants are used. However, since it is better to avoid unreacted sulfur or sulfur compound, it may be desirable to use excess phosphonate. I prefer to use up to about 5% excess (by weight) for reasons of economy, up to 20% excess can be used without adverse effect. Furthermore, to assure complete neutralization of the acid formed, a like excess of amine can be used. Although I prefer not to use solvent, one may be used if desired. When used, the solvent may be selected from, for example, hydrocarbons or ethers.

Phosphonates useful in the invention, include those in which Ar is phenyl, naphthyl, anthryl, tolyl, xylyl, ethylphenyl, butylphenyl, hexylphenyl, octylphenyl, including the tertiary octyl, nonylphenyl, decylphenyl, dodecylphenyl and tetradecylphenyl. The phosphonates in general can be made by any method known to the art, but are more often made by the reaction of 2 equivalents of phenol, for example, with 1 equivalent of phosphorus trichloride, followed by hdrolysis or reaction with alcohol. See U.S. Pat. No. 3,583,915, incorporated herein by reference. Useful amines include the primary, secondary and tertiary amines in general, but more particularly include the mono-, di- and trimethylamines, mono-, di- and triethylamines, mono-, di- and tributylamines, mono-, di- and trioctylamines, mono-, di- and tridecylamines, mono-, di- and tritetradecylamines, mono-, di- and trioctadecylamines and momo-, di- and trieicosylamines, as well as those derived from fatty acids, such as oleylamine and naturally occurring amines.

The compounds made by the process of this invention may be used with lubricating oils as antiwear additives to the extent of from about 0.1% to about 10% by weight of the total composition. Furthermore, other additives, such as detergents, antioxidant, other antiwear agents, viscosity index improvers, pour depressants, dispersants, and the like may be present. These can include phenates, sulfonates, succinimides, zinc dithiophosphates, polymers, calcium and magnesium salts and the like.

The lubricants contemplated for use with the compounds produced herein include mineral and synthetic hydrocarbon oils of lubricating viscosity, mixtures of syntnetic oils, mixtures of mineral oils and synthetic oils and greases from any of these. The synthetic hydrocarbon oils include long-chain alkanes such as cetanes and olefin polymers such as oligomers of hexene, octene, decene, and dodecene and the like.

The products made may be especially effective in synthetic oils formulated using mixtures of synthetic oils include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids. These synthetic oils can be used alone or they can be mixed with a mineral or synthetic hydrocarbon oil.

Having described the invention in broad, general terms, the following are offered as specific illustrations (Examples 1 and 2) and as a comparison (Example 3). It will be understood that the illustrative examples are not meant to limit the invention to those conditions shown.

EXAMPLE 1

To a stirred mixture of 48.7 g, 0.1 mol, of di(nonylphenyl)phosphonate and 3.06 g, 0.095 mol., of elemental sulfur were added 28.0 g, 0.105 mol, of oleylamine. The addition of amine was begun at 90° C. and was continued at a rate sufficient to cause the temperature to rise to 120° C. External heat was applied, after the addition was completed, to maintain the temperature within the range of from about 120° C. to about 125° C. for 30 minutes. Conversion of sulfur was quantitative, and no precipitation of sulfur occurred on cold storage (5°C.) overnight. The phosphorus-31 NMR spectrum indicated a mixture containing 87.4% of desired product. This is shown by the following:

TABLE 1

| Phosphorus-31 NMR Chemical Shift, (ppm) (33% in CDCl3) | Percent Area | Assignment |
| --- | --- | --- |
| 56.3 | 1.6 | Unknown impurity |
| 53.3 | 6.5 | Unknown impurity |
| 49.1 | 87.1 | Product of Example 1 |
| 45.7 | 1.4 | Unknown impurity |
| 1.8 | 3.1 | 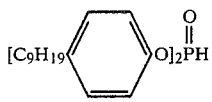 |

EXAMPLE 2

The process of Example 1 was repeated, except that 304 g (0.625 mol) of di(nonylphenyl)phosphonate, 19 g (0.59 mol) of elemental sulfur and 175 g (0.65 mol) of oleylamine were used. 492 g of product were obtained. This product was 87.9% pure by phosphorus-31 NMR.

EXAMPLE 3

This Example illustrates the necessity of adding the amine last. A mixture of di(nonylphenyl)phosphonate (48.7 g, 0.1 mol), oleylamine (28 g, 0.105 mol) and sulfur (3.2 g, 0.095 mol) was heated to 122° C., and maintained at 122° to 125° C. with stirring for 30 minutes. Sulfur precipitated from a 50% hexane solution of the product on storage in the refrigerator (5°C.) overnight, indicating incomplete reaction. The phosphorus-31 NMR spectrum indicated that only 4.5% of the desired product was formed, and 24.6 of the di(nonylphenyl)phosphonate had not reacted.

TABLE 2

| Phosphorus-31 NMR Chemical Shift, (PPM) (33% in CDCl3) | Percent Area |
| --- | --- |
| 63.4 | 4.7 |
| 56.3 | 39.3 |
| 53.3 | 23.1 |
| 49.1* | 4.5* |
| 41.0 | 3.8 |
| 1.8 | 24.6 |

*Compare the same line in Table 1, i.e., the same NMR line, 49.1

I claim:
1. A process for preparing a compound of the formula

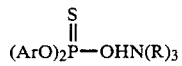

wherein Ar is an aromatic group or an aliphatic-substituted aromatic group containing 6 to 20 carbon atoms and R is hydrogen or a C to C$_{20}$ hydrocarbyl group, at least one of the R groups being hydrocarbyl, said process comprising the steps of first mixing a diarylphosphonate of the formula

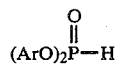

wherein Ar is as defined herein, with elemental sulfur or a sulfur-containing compound capable of forming the P=S bond, and subsequently after said step of mixing, reacting the mixture with an amine of the formula

N(R)₃ wherein R is as defined herein.

2. The process of claim 1 wherein the hydrocarbyl group is an alkyl, a cycloalkyl, an alkenyl or a cycloalkenyl group.

3. The process of claim 1 wherein the aliphatic group is an alkyl group.

4. The process of claim 2 wherein the hydrocarbyl group is an alkyl group.

5. The process of claim 3 wherein the alkyl group is a methyl, ethyl, butyl, hexyl, octyl, decyl, dodecyl, or dodecyl group.

6. The process of claim 4 wherein the alkyl group is a methyl, ethyl, butyl, octyl, decyl, tetradecyl, octadecyl or eicosyl group.

7. The process of claim 1 wherein the amine is oleylamine.

8. The process of claim 1 wherein Ar is a phenyl, naphthyl, anthryl, tolyl, xylyl, ethylphenyl, butylphenyl, hexylphenyl, octylphenyl, nonylphenyl, decylphenyl, dodecylphenyl or tetradecylphenyl group.

9. The process of claim 8 wherein the octylphenyl group is the tertiary octylphenyl group.

10. The process of claim 1 wherein the amine is a mono- di- or trimethylamine, mono- di- or triethylamine, mono-, di- or tributylamine, mono-, di- or trioctylamine, mono-, di- or tridecylamine, mono-, di- or tritetradecylamine, mono-, di- or trioctadecylamine or mono-, di- or trieicosylamine.

11. The process of claim 1 wherein the sulfur containing reactant is elemental sulfur.

12. The process of claim 1 wherein the temperature of reaction is selected from the range of from about 25° C. to about 175° C.

13. The process of claim 12 wherein the temperature of reaction is from about 115° C. to about 175° C. when a reactant is elemental sulfur.

14. The process of claim 1 wherein the reactants are di(nonylphenyl)phosphonate, elemetal sulfur and oleylamine.

* * * * *

UNITED STATES PATENT AND TRADEMARK OFFICE
CERTIFICATE OF CORRECTION

PATENT NO. : 4,600,543

DATED : July 15, 1986

INVENTOR(S) : Robert F. Bridger

It is certified that error appears in the above-identified patent and that said Letters Patent is hereby corrected as shown below:

Column 2, line 44, after "90°C" insert --to about 125°C--.

Column 2, line 66, "hdrolysis" should read --hydrolysis--.

Column 4, line 58 (claim 1), "$C_{to}$" should read --$C_1$ to--.

Signed and Sealed this

Ninth Day of December, 1986

Attest:

DONALD J. QUIGG

Attesting Officer

Commissioner of Patents and Trademarks